United States Patent [19]
van der Valk

[11] Patent Number: 5,163,449
[45] Date of Patent: Nov. 17, 1992

[54] DEVICE FOR A MALE CONDOM, AND A CONDOM TO BE USED WITH THIS DEVICE

[76] Inventor: Willem L. van der Valk, 11 E. 92nd St., Apt. 3F, New York, N.Y. 10128

[21] Appl. No.: 616,451

[22] Filed: Nov. 20, 1990

[30] Foreign Application Priority Data

Nov. 21, 1989 [NL] Netherlands .......................... 8902873

[51] Int. Cl.⁵ ................................................ A61F 6/04
[52] U.S. Cl. ...................................... 128/844; 128/918
[58] Field of Search .................. 128/842, 844, 79, 918; 604/330, 347–353

[56] References Cited

U.S. PATENT DOCUMENTS

| | | | |
|---|---|---|---|
| 2,591,783 | 4/1952 | Craddock | 128/842 |
| 2,904,041 | 9/1959 | Brown | 128/842 |
| 3,536,066 | 10/1970 | Ludwig | 128/844 |
| 4,664,104 | 5/1987 | Jaicks | 128/844 |
| 4,735,621 | 4/1988 | Hessel | 128/844 |
| 4,794,920 | 1/1989 | Robichaud | 128/844 |
| 4,834,113 | 5/1989 | Reddy | 128/844 |
| 4,856,534 | 8/1989 | Sorkin | 128/844 |
| 4,875,491 | 10/1989 | Parrone | 128/844 |
| 4,888,007 | 12/1989 | Loeb | 128/844 |

FOREIGN PATENT DOCUMENTS 0232797 3/1911 Fed. Rep. of Germany .

*Primary Examiner*—Robert A. Hafer
*Assistant Examiner*—Michael Brown
*Attorney, Agent, or Firm*—Cornell D. M. Judge Cornish

[57] ABSTRACT

A device for use with a male condom that has a substantially rigid ring with a substantially axial width and a radial thickness, an internal diameter of such dimensions that it fits loosely around the male organ when erect, the ring is provided with an attachment device for releasable connection with the open end of the condom, the ring has a peripheral groove along its outer surface and the diameter of the ring on one side of the groove is slightly greater than on the other side.

20 Claims, 7 Drawing Sheets

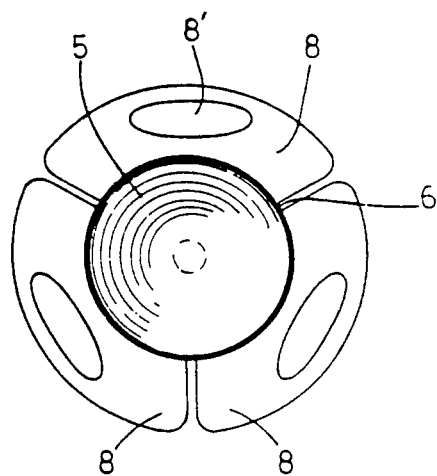
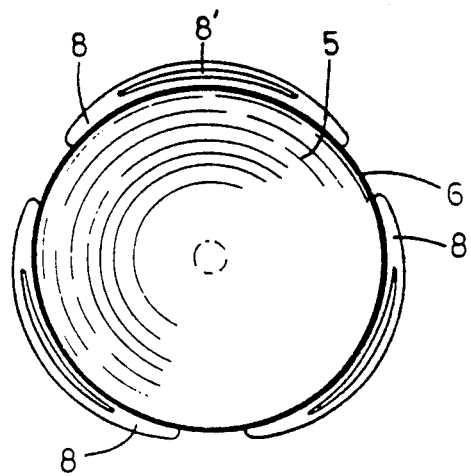
FIG. 4a          FIG. 4b
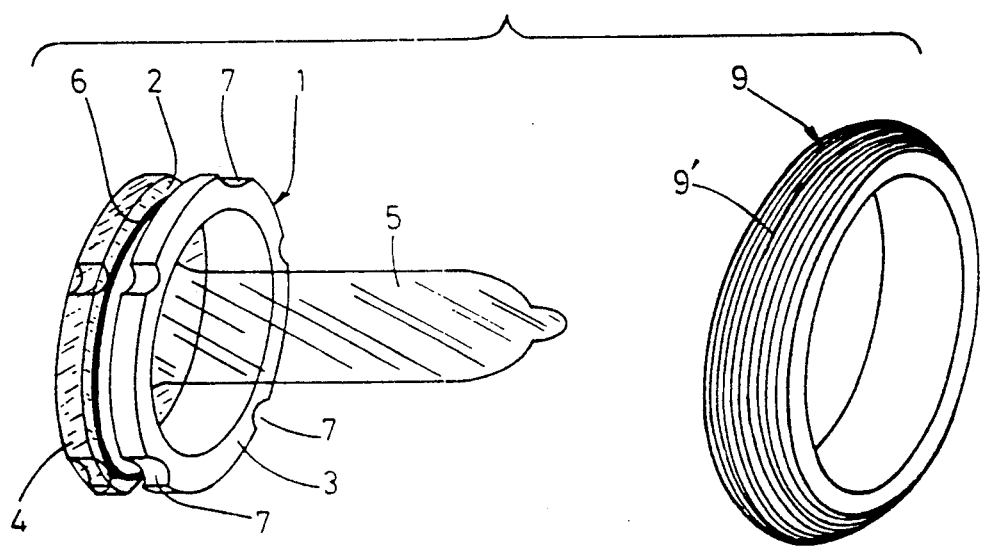
FIG. 3

DEVICE FOR A MALE CONDOM, AND A CONDOM TO BE USED WITH THIS DEVICE

The invention relates to a device for a male condom as well as a condom to be used with this device. Note: the "male condom" referred to herein is the conventional pre-rolled condom in contrast to the "female condom" which is placed in the vagina prior to coital penetration as recently proposed by Hessel in U.S. Pat. No. 4,735,621.

Condoms are currently in great use to block the transfer of undesirable bodily fluids during intercourse and thus prevent pregnancy and the spread of contagious diseases. However, the use of condoms is often experienced by mean as annoying and as sexually unappealing, and in addition condom use also carries with it several risks.

The purpose of the present invention is to ameliorate this situation by providing a device to be used with the male condom which will afford a more natural feeling during intercourse and also increase the safety of condom use.

To this end the device to be used with a male condom according to this invention is characterized by a substantially rigid ring of substantial axial width and/or radial thickness and with sufficient internal diameter that this will fit loosely around the male organ when erect, and in addition, the ring is equipped with attachment means for a releasable connection with the open end of the condom.

The device offers a number of important advantages.

With respect to enhancing the natural feeling for the male during intercourse the ring offers the advantage that it relieves the irritating pressure on the penis created by the elastic band at the open end of the conventional pre-rolled condom currently in use by having this open end of the condom attached to the ring which fits loosely around the erect penis. The ring is kept in place by the condom itself which fits snuggly around the penis, or by other means. By eliminating the local pinching pressure of the condom's elastic band the outer skin of the penis can move more freely during intercourse with respect to the penis itself which causes increased stimulation for the male (as would be the case without a condom). Also to the degree that the evenly spread pressure of the condom on the penis is experienced as pleasurable, this feeling is enhanced by the elimination of the local pinching pressure of the elastic band. Further the ring will act to keep the condom evenly stretched along the length of the penis thereby eliminating the possibility that creases (and folds) or the like reduce the transfer of feeling to the penis.

Another sensation enhancing possibility offered by the ring is the creation of a quasi-vaginal effect in the male condom, whereby as it were a "semi-form fitting" condom is created. If the condom is (a) provided with a lubricant on its inner surface and (b) chosen so that its length is lightly shorter that that of the erect penis, then during the forward movement of the penis into the vagina at a certain point the ring's forward progress will be arrested as it is blocked by the entrance of the vagina, after which any further foreward movement of the penis will cause the condom to be stretched along its length between the tip of its open end and the ring, thereby creating a rubbing friction between the inner condom wall and the skin of the penis which will create a favorably stimulating and natural sensation for the male. In this way both male and female will experience a more natural movement and friction stimulation of the sexual organs, which cannot be realized in the currently known male and female condoms.

In addition the ring itself can enhance the stimulation of male and female through the axial pressure on the respective sexual organs and the surrounding areas at the end of the penetration movement of the male, whereby the ring as it were acts to simulate the pressure of the respective pubic bones.

The ring is also safety enhancing, in that the condom is prevented from slipping off the penis and escaping into the vagina. For the ring by the very bulk of its dimensions will remain outside the vagina and so too the open end of the condom will remain outside of the vagina, and thus even in the eventuality that the condom should slip off the penis, fluids would not enter the vagina from the condom directly. When the penis is withdrawn from the vagina after ejaculation, either male or female can readily grasp the ring thus preventing the condom from remaining in the vagina.

A preferred embodiment of the device according to the invention is characterized in that the ring is provided with a peripheral groove along its outer surface.

This feature makes it possible to easily attach the conventional pre-rolled condom to the ring in such a way that the elastic band at the open end of the condom will come to rest securely in the groove of the ring. Thus the condom can be drawn from one side of the ring and pulled directly over the outside of the ring until the elastic band is positioned in the groove; it is also possible to first pass the open end of the condom through the inside of the ring and then stretch the open end of the condom over the outside of the ring and then place the elastic band in the groove. By these two methods of applying the condom to the ring it is possible to create two different effective condom lengths, whereby it is possible through experimentation to determine the proper condom length in order to create the optimal quasi-vaginal effect. It is also possible to provide the ring with two or more grooves, in order thus to be able to more finely adjust the effective condom length.

Obviously care should be taken in determining the exact shape of the ring so that no points of contact between ring and condom could result in tearing (or otherwise damaging) the condom. By giving the ring the proper shape, this danger can be kept to a minimum, and indeed smaller than the possibility that the condom will tear in other places. The shape of the ring can also be chosen to contribute to the enhancement of pleasure in use such as by creating properly rounded edges, ribbed surfaces, etc.

In order to make is easier to attach the condom to the ring, it may be desirable to provide the ring with a number of finger-tip-indentations, preferably five, regularly spaced around the outer surface of the ring.

These finger-tip-indentations would assist in grasping the ring when placing the elastic band of the open end of the condom in the outer groove. With pre-rolled packaged condoms currently in use the condom should first be rolled down the partially, or fully, erect penis after which the elastic band at the open end of the condom is attached to the ring which is held near the base of the penis.

Condoms with lubricants can be slippery to handle, in such cases it can be difficult to place the elastic band at the open end of the condom in the groove of the ring. In order to simplify the attachment of the open end around the ring, the invention also envisions a condom, to be used with the ring. which provides a number of tabs, loops or the like attached around the circumference of its open end, so that the fingers can readily grasp the open end of the condom thereby facilitating the placement of the open end around the ring and into the groove. Elastic loops or tabs with holes therein are preferred because the fingers can be passed through them in order to attach the condom, and in addition when the open end of the condom is stretched around the ring also the loops will be so stretched as to lie entirely within the groove of the ring.

In the preferred embodiment the ring has an axial width of at least eight millimeters and a radial thickness of at least seven millimeters, in addition it is advantageous to adapt the shape of the ring to the body contours, of principally the female in order to achieve an optimal external stimulation of the area surrounding the vagina. Thus it is preferred that the cross-section be oval-shaped while also allowing the axial width of the ring to vary around its periphery. Also the hole through the ring can be placed at an angle with respect to the outer surface of the ring.

In such an oval variant the ring shall be placed around the penis in such a way, that the major axis of the oval will be placed in the upward direction, while the axial width of the ring will be greater on the lower side of the ring than on the upper side. In spite of the fact that the ring fits loosely around the penis it is held in the above mentioned position by the radial tension which the condom, snugly attached to the penis, exerts on the ring.

The ring can also be provided with an elastic band which can be removably attached, for example, in an extra groove added for this purpose and which can be detached and allowed to slip onto the condom at a place near the ring in order to clamp the condom firmly against the penis as it softens after ejaculation and thus prevent any escapement of fluids from the condom. The band can be provided with tabs or loops to make it easier to maneuver it.

The invention also contemplates an auxiliary ring which has a larger diameter than the firstnamed ring, hereafter also called the basic ring, and which can be removably attached to the basic ring.

The auxiliary ring offers a number of advantages. In combination with the basic ring which has the groove around the outer circumference, the auxiliary ring offers the advantage that the outer diameter of the basic ring can be kept small enough so as not to excessively radially stretch the open end of the condom, while the auxiliary ring can be given a diameter large enough to ensure that the ring combination will not penetrate the vagina. For condoms currently in use the radial stretching of the open end of the condom to a diameter of about 65 to 70 millimeters is considered a safe limit. However, the auxiliary ring can, without difficulty, be chosen with an even larger diameter. A larger diameter might also be desirable in order to stimulate the clitoris of the female by the pressure produced by the auxiliary ring during the penetration movements of the male. It is preferable that the connection between the basic and auxiliary rings is such that fluids are prevented from passing between the rings.

The auxiliary ring can also be designed to have a greater axial width than the basic ring in order to curtail the dept of penetration by the penis into the vagina. [For example, to prevent injury or irritation to the cervix in cases where the erect penis is too long relative to the depth of the vagina.]*

The auxiliary ring can also be designed to provide a protective shield to cover the outside surface of the basic ring around which the condom is stretched in order to protect the stretched surface of the condom from being damaged by rubbing or pounding against the skin of the male or female.

The auxiliary ring can also serve as a basis to attach other devices to the ring. Thus for example an "apron" can be attached to the auxiliary ring by means of a rubber attachment band. The apron could consist of a rather thick (for example 1 mm) through pliable, washable and reusable material and functions as a partition between the genital areas of the male and female, thus serving to prevent an exchange of bodily fluids.

The auxiliary ring can be attached to the basic ring in a variety of ways, such as by a snap-on attachment or a clamp attachment. It is obviously essential that the auxiliary ring remain firmly attached to the basic ring during coitus.

Instead of the above described auxiliary ring it is also possible to use a plate-like element, of greater radial extent although of lesser thickness and removably attachable, which would serve as a type of substitute for the auxiliary ring and apron combination.

The basic ring, the auxiliary ring and/or the plate-like element can be constructed of artificial materials. It is important, however, that the rings be readily washable, in order to insure their hygenic reusability. It may be possible to cover the basic ring, the auxiliary ring and/or the plate-like element with skin-like material in order to foster a more natural feeling when contact is made with the skin.

In order to keep the ring properly attached to the body of the male, it is considered useful to introduce a type of open underpants or girdle-like or similar construction to which the ring can be removably attached. On the other hand it is also possible to have the ring secured to the body of the female, whereby the ring could be coupled to an "attachment ring" which would be affixed to the body of the female by a girdle-like or a multiple-band construction. In this case the ring—having already been properly attached to the condom covering the penis—would upon the penis penetrating the vagina be snaped to the attachment ring already affixed to the female. After intercourse the basic ring would be detached from the attachment ring and would be removed simultaneously as the penis is withdrawn from the vagina.

Obviously it is possible to attach the condom to the basic ring in other ways than described above. For example (in one embodiment), a modified condom is proposed possessing a thin, widened collar at its open end, which could be snapped onto the basic ring of attached thereto by sandwiching it between the basic ring and an additional snapring to lock it in place. It is preferred that in this case the condom be packaged in such a way that it be folded up in a zig-zag fashion and be supplied with a lubricant, at least on its inner side.

The above embodiment offers the advantage that the condom can first be attached to the ring, after which the penis is passed through the ring and condom, thus permitting the ring and condom to be placed on the penis in a single operation.

In all of the embodiments of the invention described above the ring is always meant to be reusable. It is however, conceivable to have an embodiment of the plate-like ring constructed in a way that the plate-like element is integral with the condom, and thus would be intended for one-time use only. In this case the condom would again be packaged in zig-zag folded fashion and be supplied with a lubricant, at least on its inner side. Also in this connection it should be noted that the term "ring" is meant to include a thin plate-like element with a hole therein.

To increase the safety with respect to the possible undesirable exchange of body fluids, the invention proposes to provide a fluid absorbing pad that is impregnated with a spermicidal and disease killing substance which can be removably attached to the ring, the auxiliary ring or the plate-like element. Similar considerations have led to the idea of a ring-like absorbant pad which is adapted to fit around the base of the penis near the ring and under the condom and which similarly is capable of readily absorbing body fluids and is impregnated with spermicidal and disease killing agents, thus serving to absorb and/or neutralize any fluids should these nevertheless escape from the open end of the condom.

Further characteristics and advantages offered by the invention will be apparent from the descriptions of the drawings which follow and which show schematically a number of embodiments of the invention by way of example.

FIG. 3 shows a perspective of the basic ring, a condom placed on it and an auxiliary ring of the device according to the invention.

FIGS. 4a and 4b are axial views of a male condom according to the invention in a non-stretched and a radially stretched position, respectively.

The figures show various aspects and embodiments of the device for a male condom.

Figure 1:
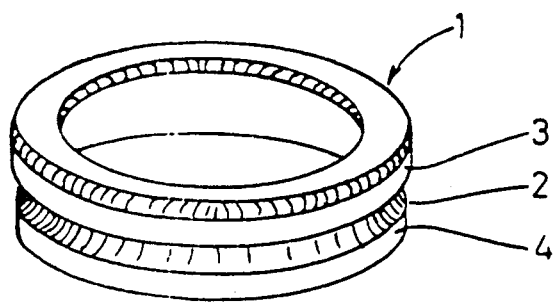
FIG. 1 shows a perspective view of the basic ring of the device for a male condom according to the invention.
Figure 2:
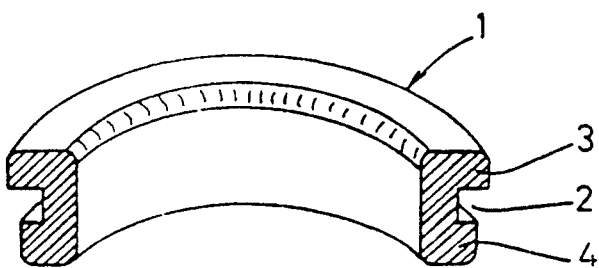
FIG. 2 is a perspective cross-sectional view of the basic ring of the device for a male condom according to the invention.

Turning especially to FIGS. 1 and 2 where the basic ring 1 is shown. This basic ring 1 possess an inner diameter of such dimensions, that it fits with play around the erect penis. For example, this inner diameter could measure 50 mm, though it could also be chosen to be larger or smaller, or preferably be executed in different sizes. In addition the basic ring 1 possesses means for attaching to it a male condom 5 (see FIG. 3). For currently used condoms which are made of thin elastic material and possess a closed end and an open end with an elastic band 6 usually attached to the open end (see FIGS. 3,6,7) the preferred attachment means consists of a peripheral groove 2 extending circumferentially along its outer surface. The groove 2 divides the ring into two axial parts, in this case the greater part 3 and the smaller part 4, wherein the greater part 3 possesses a slightly larger diameter than the smaller part 4.

Figure 6:
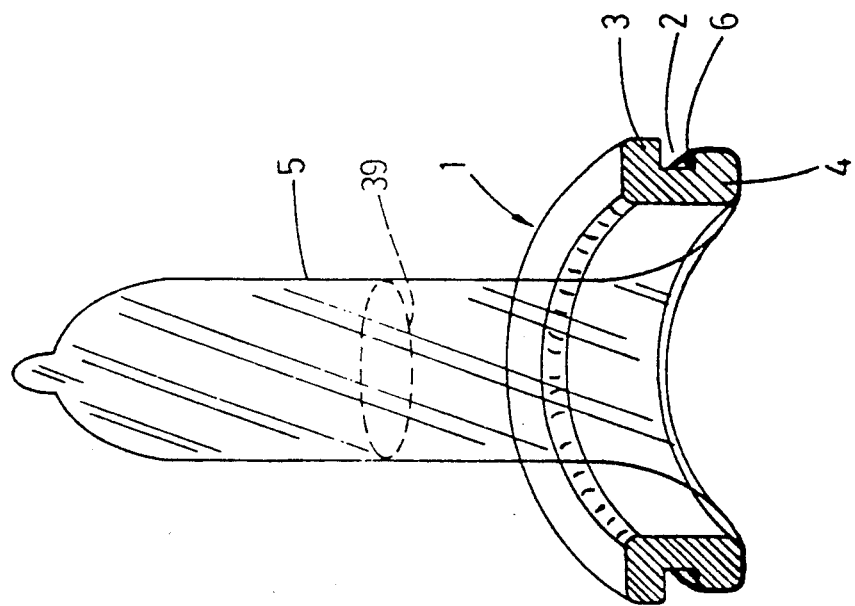

FIGS. 3 and 6 show the most usual method of attaching the condom 5 to the the basic ring 1. First, the condom is passed through the inside of the ring, then the elastic band 6 on the open end of the condom 5 is pulled back over the part 4 of the basic ring 1 until the elastic band 6 rests securely in the groove 2 of the basic ring 1. Using conventional pre-rolled condoms this means that in practice the condom 5 is first completely rolled down the erect penis, after which the basic ring 1 is placed over the penis until it rests near the open end of the condom, and then the elastic band 6 of the condom 5 is pulled over the basic ring 1 until it rests in the groove 2.

The groove 2 chould be so dimensioned that on the one hand it securely attached the elastic band 6, and on the other hand it is easy to clean. The inner part of groove 2 could thus be rounded.

To fascilitate the handling of the basic ring 1 when affixing the condom, the basic ring 1 is provided with a number of finger-tip-indentations 7 (FIG. 3). These finger-tip-indentations 7 can be introduced on only part 3 of the basic ring 1 and thus on only one side of the groove 2 or they can be placed on both prts 3 and 4, and thus on both sides of groove 2. In principle two finger-tip-indentations 7 one each for thumb and index finger should suffice, though five finger-tip-indentations 7 are preferred so that the basic ring 1 can be held in different positions, and with either hand, so that at all times the thumb and index finger (of either hand) can grasp the two indentations that are nearly diametrically opposed to each other. Thus more than half of the ring is kept free to enable the other hand to place the elastic band 6 of the condom 5 into the groove 2.

As is apparent from the above description, the basic ring 1 can readily be used in combination with the currently used condom as shown in FIGS. 3 and 6. To further fascilitate the attaching procedure, the condom itself can be adapted according to the invention by providing a number of tabs (with or without holes), or loops or the like attached around the circumference of its open end, and these tabs, loops and the like can be readily grasped with the fingers in order to pull the elastic band 6 of the condom over the basic ring 1. FIG. 4a schematically shows the open end of such a condom 5, in which three tabs 8, with holes 8' through which the fingers can be passed, are provided around the circumference of the elastic band 6. FIG. 4b shows the same open end of the condom 5 as in FIG. 1a, through in this case the elastic band 6 rests in the groove 2 of the basic ring 1 and thus is now circumferentially stretched, and indeed in such a way that the tabs 8 are also stretched and thus lie along side the elastic band 6 without protruding from the groove 2.

A further adaptation of the condom consists in providing the area adjacent to the open end of the condom 5 with a greater wall thickness than of the remaining portion of the condom. For example, from the open end to a distance of about 2 to 3 cm the wall can be made about 15 times thicker and then be allowed to gradually taper off to the thickness of the remaining portion of the condom. When used with the ring, the thickened wall portion of the condoms 5 will thus lie on, and completely surrounding a portion of the basic ring 1, and because of its greater strength will further lessen the possibility that condom 5 will tear due to radial stretching, in comparison to convetional condoms without this reinforcement.

In the above embodiments the basic ring 1 possesses a round cross-section, in which the inner circumference and outer circumference are coaxial and the axial width is constant over the entire circumference. However, the basic ring 1 can also possess a shape other than being round, such as an oval shape with the inner and outer circumference of the basic ring 1 being adapted to the body contours of the male and female. Also with the same objective in mind, the axial width of the basic ring 1 can vary around the circumference. In addition, instead of being solid, as in the earlier descussed embodiments, the basic ring 1 can be given a hollow consistency, although it must be assured that the ring in use will possess a degree of rigidity or stiffness in order to be certain that the condom will remain firmly secured to the ring and that the open end of the condom be maintained in a radially stretched position. Obviously the basic rind 1 should possess rounded edges to prevent injury to the skin and provide a pleasing sensation.

According to the invention the choice for a male condom can also include an auxiliary ring 9, which possesses a larger diameter than the basic ring 1. In most cases the auxiliary ring 9 will be attached around the basic ring 1. The auxiliary ring 9 can be attached to the basic ring 1 in a variety of ways, though the simplest manner is obviously by clamping the auxiliary ring 9 onto the basic ring 1. In this case, as was indicated earlier, part 3 of the basic ring 1 is provided with a slightly larger diameter than part 4, so that the inner surface of the auxiliary ring 9 can clamp onto the outer surface of part 3 of the basic ring 1, as shown in FIGS. 3, 5, 7 and 8. The outer surface of part 4 of basic ring 1 is to be kept at such a distance from the inner surface of the auxiliary ring 9, that the outside surface of condom 5 placed on part 4 will not make contact with auxiliary ring 9 and hence will not risk being damaged by it.

In the embodiment of auxiliary ring 9 shown in FIG. 3, the main object of the auxiliary ring 9 is to achieve an enlargement of the diameter of the basic ring 1 and auxiliary ring 9 combination in order to insure that the ring and hence the open end of condom 5 should ever enter the vagina. Obviously the diameter of the basic ring 1 could be enlarged to achieve this. However, with the earlier described attachment methods for attaching the condom 5 to the basic ring 1 this would require a greater radial stretching of the open end of the condom 5 than is considered safe. With condoms currently in use, the stretching of the elastic band 6 at the open end of condom 5 to fit over a ring with a diameter of about 65-70 mm is considered an outer limit Note: placing the condom 6 on the ring 1 itself requires stretching the condom even further, while the need could arise for a ring with a larger diameter, say of 80 mm. In this case the basic ring 1 could be given a diameter of 65 mm, while the auxiliary ring 9 could be given an outer diameter of 80 mm. This larger total diameter of the basic ring 1 and auxiliary ring 9 combined with the substantial (axial) width of at least the auxiliary ring 9 offers the attendant advantage that the area of the clitoris of the female is stimulated by the pressure of the auxiliary ring 9 exerted on it during the penetration movements of the male. The outside surface of the auxiliary ring 9 can be so designed that this will have a pleasant and stimulating affect. It is preferred that at least the side of the auxiliary ring 9 which during use faces the female will possess rounded contours and possibly be provided with ridges running in the circumferential direction.

Figure 5:
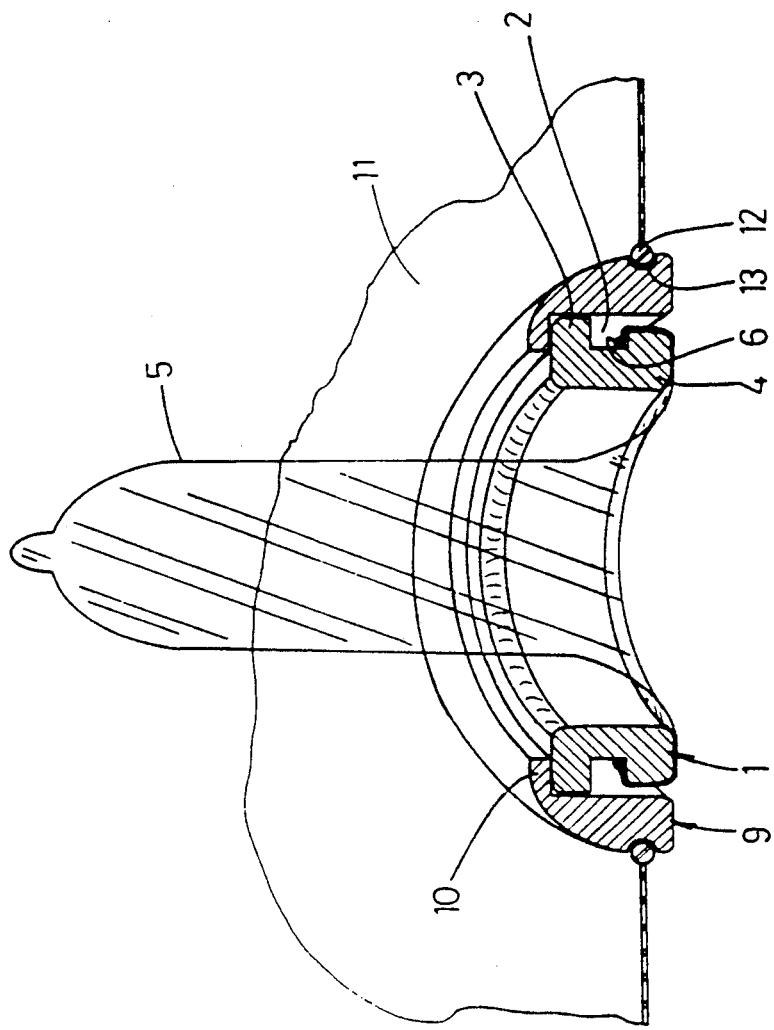
FIG. 5 is a perspective cross-sectional view of a basic ring with a condom attached to it, an auxiliary ring connected to it and an apron, surrounding and attached to the auxiliary ring, of the device according to the invention.

FIG. 5 shows a somewhat altered embodiment of the auxiliary ring 9, having a greater axial width than the basic ring 1 and possessing an internal shoulder to hold the basic ring 1, which has been pushed into the auxiliary ring 9. In this embodiment the auxiliary ring 9 also serves as a "staging base" onto which additional devices can be attached, such as the apron 11, shown in FIG. 4, which consists of a piece of pliable and somewhat elastic material which is attached to the auxiliary ring 9 by an elastic band 12 encircling a hole positioned in the apron 11, whereby the elastic band 12 attaches itself securely to a circumferential groove 15 on the outer surface of the auxiliary ring 9. The apron 11 serves as a barrier between the male and female genital areas during intercourse, in order to prevent the exchange of body fluids.

As an alternative to the combination of the auxiliary ring 9 with apron 11 one could also choose for a plate-like element attached to basic ring 1.

Figure 7:
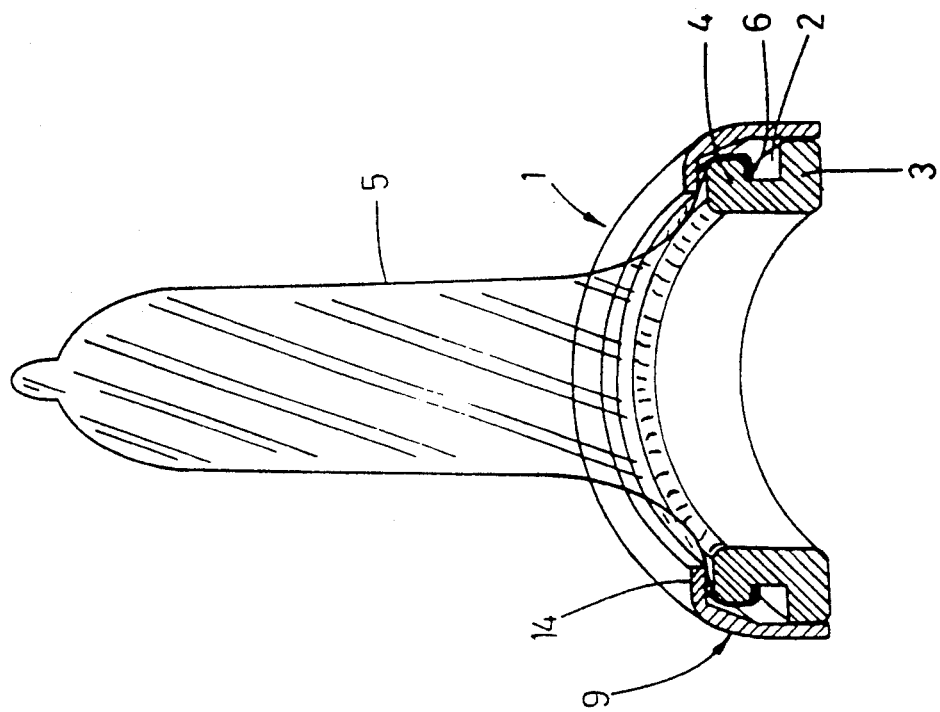
FIGS. 6 and 7 show a perspective cross-sectional view of two ways of attaching the condom to the basic ring of the device according to the invention.

FIG. 7 shows a further variation of the embodiment of auxiliary ring 9 which in this case is provided with a protection ring, which serves to cover those portions of the basic ring 1 which are in contact with the condom 5. This is especially desirable when condom 5 is attached to the basic ring 1 in ways other than shown in FIG. 5. In the situation shown in FIG. 7 the positioning of the basic ring 1 is reversed, so that condom 5 is not first passed through the inside of the ring, but instead is pulled directly over the outside and attached to part 4 of the basic ring 1. By attaching the auxiliary ring 9 as shown in FIG. 7 its flange 14—which covers with some room to spare part 4 of the basic ring 1 so that it does not pinch or touch the condom—will make contact with the skin of the female and thereby protect the condom.

It should also be mentioned with respect to FIGS. 5, 6 and 7, as has been done earlier, that the two methods of applying condom 5 to the basic ring 1 allow various effective lengths of condom 5 to be realized which is of interest for obtaining the proper condom length in order to achieve the so called quasi-vaginal effect in the condom 5. Obviously it would be most desirable to have condoms readily available in various, and preferably a great number of, sizes with respect to both length and diameter in order thus to be able to select the appropriate condom for a given penis length and thickness.

Through the quasi-vaginal effect within condom 5 in which its elastic band 6 is attached to the basic ring 1 and thus allowing the condom to move independently of the penis and with each penetration movement of the penis the condom will be stretched in the vagina between the end of the penis and the portion attached to the basic ring 1, and thus the condom wall will move locally with respect to the penis causing a frictional stimulation it would, in principle, be possible for the condom to be made thicker than is currently customary. This would strengthen the condom and thus make it more appropriate for multiple use, which would offer the user financial benefits without endangering the safety of the condom.

Figure 8:
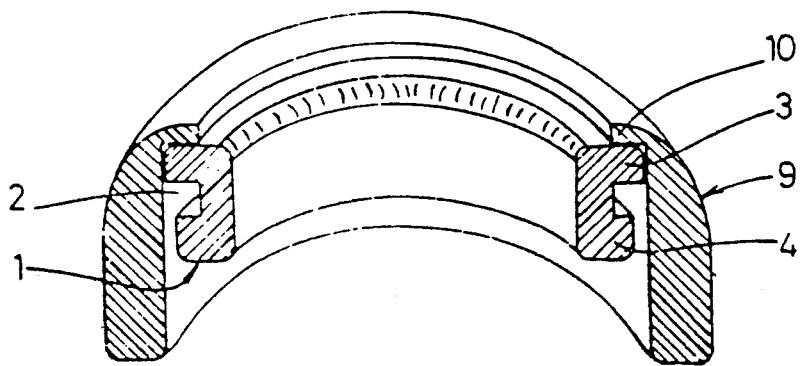
FIG. 8 is a perspective cross-sectional view of a basic ring and an auxiliary ring attached to it as an augmentation (or "distancing") ring embodiment of the auxiliary ring of the device according to the invention.

FIG. 8 shows a further embodiment of the auxiliary ring 9 which is designed as a "distancing" ring and serves to curtail the maximum depth of penetration of the penis in the vagina. To this end the auxiliary ring 9 possess a substantially greater axial width than the basic ring 1, for example 26 mm or greater as opposed to 8–20 mm for the basic ring 1. Limiting the maximum penetration depth of the penis in the vagina can be important should it cause discomfort to the female or should she not be in a condition to take in the entire penis. By attaching the auxiliary ring 9 with a greater axial width a part of the penis will be kept outside of the vagina. In this case the basic ring 1 can be attached to the auxiliary ring 9 by a snap mechanism, which maintains contact between the basic ring 1 and the inward turned flange 10 of the auxiliary ring 9.

Figure 9:
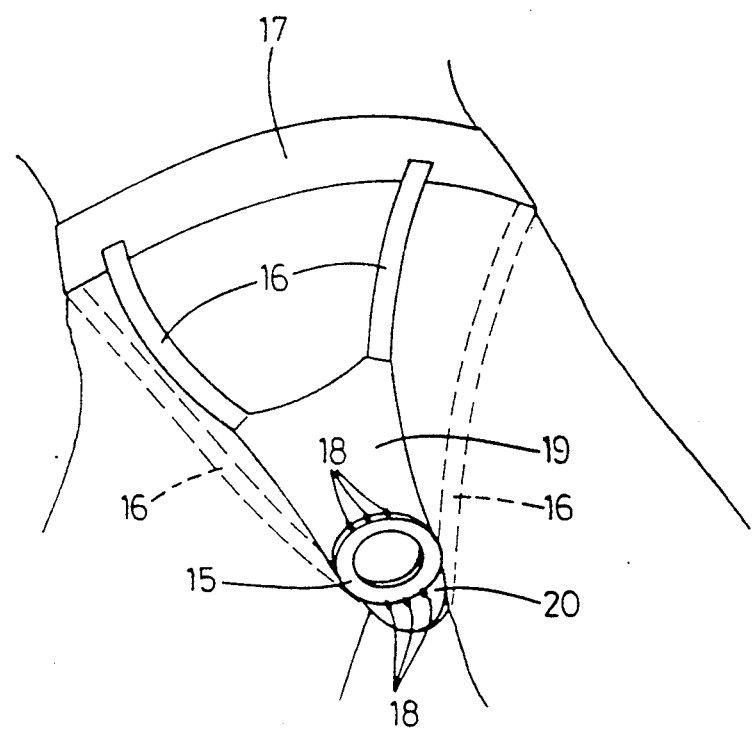
FIG. 9 is a perspective view of an attachment ring attached to a female of the device according to the invention.

FIG. 9 shows an additional device that can be used in combination with the basic ring 1, consisting of an attachment ring 15 which can be attached to the body of the female by means of a girdle construction so that the attachment ring 15 will be positioned at the opening of the vagina. In the embodiment shown the girdle construction consists of four bands 16, which are attached to a waist band 17. Around the circumference of the attachment ring 15 are provided snap organs 18 or the like with which the basic ring 1 can easily be attached to and released from the attachment ring 15. In this way the basic ring 1 can be fixed to the body of the female. Thus once the penis covered by the condom on enters the vagina, the basic ring 1 would be snap attached to the attachment ring 15. Additionally a cover could be placed on the attachment ring 15, which after withdrawal of the basic ring 1 could replace it and prevent any escapement of fluids from the attachment ring 15.

On the upper and lower side of the attachment ring 15 are plate-like extensions 19 and 20, respectively, which block fluids between male and female and which, additionally can serve as attachment or support organs for padding material, which is fluid absorbing and is impregnated with sperm neutralizing and disease killing substances.

Figure 10:
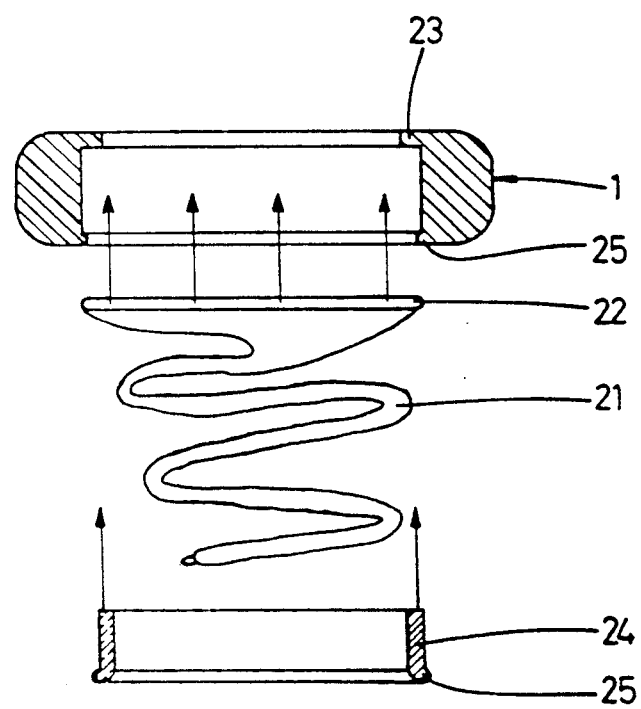
FIG. 10 is a longetudinal sectional view of the basic ring with a special male condom according to the invention.

FIG. 10 shows another embodiment of the basic ring 1 to be used with a special condom 21, which at its open end is provided with a widened (or flared) collar 22 having a certain degree of rigidity. In this embodiment the collar 22 is attached to the basic ring 1 by being clamped between an internal flange 23 and a separate snap ring 24, in which the basic ring 1 and the snap ring 24 are secured to each other by snap organs 25. Obviously other methods of attaching the condom 21 to the basic ring 1 are possible.

A further special attribute of condom 21 is that it is packaged in a zig-zag folded manner and is provided with a lubricant for the inner and outer sides of condom 21. This condom can even be attached to the basic ring 1 before application, after which it remains only to push the erect penis through ring 1 and condom 21, which can readily be done provided the inner side is sufficiently slippery. Moreover, it is also possible to have this condom 21 attached to the attachment ring 15 of the woman (FIG. 9), again prior to entry, after which the male would be able to simultaneously insert the penis into the condom 21 and the vagina.

Figure 11A:
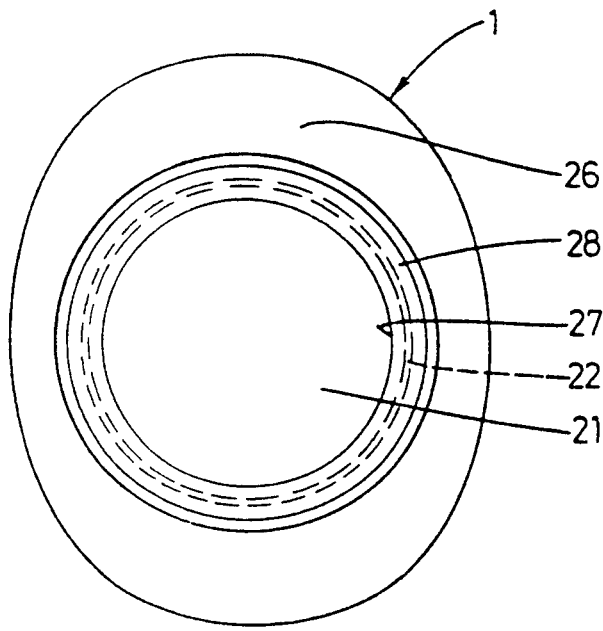
FIGS. 11a and 11b are a plane view and a longitudinal sectional view, respectively, of a non-reusable rind and a special condom.
Figure 11B:
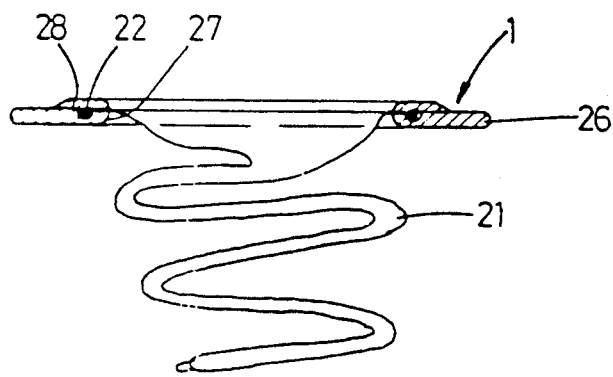

FIGS. 11a and 11b show that the embodiment of condom 21 shown in FIG. 10 could in principle also be integrally attached to the ring and thus become a condom ring combination for one-time use, in which case the ring would preferably consist of a thin plate 26 with a hole 27 in it as is shown. The condom 21 is here attached to the circumference of the hole 27 of the plate 26, for example by an attachment ring 28, wherein the condom is maintained in a folded condition by strips on both sides of the condom attached with glue on both sides of the plate. As an alternative, the condom 21 and plate 26 could also be integral, consisting of one continuous element.

The invention is not limited to the above descriptions and embodiments shown in the drawings, which can be varied in a number of ways within the scope of the invention. Thus, for example, it would be possible to design the ring with an opening, such as in the form of a horse-shoe. In such an embodiment the ring would still offer the same advantages as with a closed (or continuous) ring, namely: eliminating the pressure of the elastic band of currently used condoms; making it possible to achieve the quasi-vaginal effect with a male condom; safeguarding against the condom dislodging and slipping into the vagina; and providing the external stimulation of the genital areas.

A further possibility is the creation of an inflatable ring, which after the open end of the condom has surrounded it can be inflated to the desired shape, thereby insuring that the condom is securely attached.

Obviously embodiments of the ring without groove 2 are also possible, which would still enable the conventional male condom 5 with an elastic band 6 to be securely attached to it. Thus it is possible to provide ring 1 with a "half" groove, which would border one side of the ring 1, thus forming a ring-like end portion having a smaller diameter, and in which the elastic band 6 would rest securely in a manner similar to FIGS. 6 and 7. Also the outer surface of ring 1 can be provided with ridges running in a circumferential direction or it can be provided with a haring bone type of pattern of criss-crossing grooves and ridges or an otherwise abrasive-like surface, with a view to holding condom 5 with elastic band 6 securely in place by friction.

Furthermore, it is also possible to use condom 5 in the sense of the invention with a very simple ring, i.e. a completely smooth ring without any groove, or ridge patterns or friction causing surfaces. One possibility consists of adding either and additional elastic band or by providing a thickened, or reinforced, portion to the condom at a position of about 1 to 3 cm distant from the elastic band, a distance which roughly approximates the thickness width of the ring 1. This construction would prevent the elastic band 6 which now no longer rests in a groove from being pulled off the ring due to the slippery lubricated surface of the condom, which would result in the condom completely disengaging from the ring 1 and affixing itself to the penis. The additional elastic band or the thickened wall portion prevents this from occuring by providing a countervailing resistance to the tension exerted by elastic band 6. In addition, the condom could be manufactured with a contoured bulge in its wall at or near its open end, again, in order to be able to encompass and attach itself securely to ring 1. In addition, friction between the condom and the external surface of the ring can be increased by, for example: ensuring that the lubricants are absent from the area near the end of the condom; by providing the condom with ridges, grooves or a friction increasing pattern on the inner side of the open end of the condom; or by covering the inner side of the open end of the condom with a highly friction producing material or substance.

In addition, it is possible to use the basic ring without an actual male condom. In this case the objective for using the ring would be to stimulate the genital areas [i.e., in certain instances it could even be viewed as a kind of therapeutic device]. A tubular condom (actually a male condom from which the front end portion has been removed a "truncated condom") can serve to hold and center the ring on the penis. This condom would still exert a pressure at the base of the penis, which some men may even find pleasant, but which is obviously far less than the local pressure caused by the elastic band. The front portion of this "attachment" condom could be provided with a simple hem to prevent tearing of the condom.

I claim:

1. A device for use with a male condom characterized by a substantially rigid ring with substantial axial width and/or radial thickness and with an internal diameter of such dimensions that it fits loosely around the male organ when erect, the ring being provided with attachment means for a releasable connection with the open end of the condom, said ring has a peripheral groove along its outer surface and the diameter of the ring on one side of the groove is slightly greater than on the other side.

2. A device according to claim 1, wherein in the outer surface of the ring a plurality, preferably five, finger-tip-indentations are regularly spaced along the periphery.

3. A device according to one of the preceding claims, wherein the ring has an axial width of at least 8 mm and/or a radial thickness of at least 7 mm.

4. A device according to claim 3, wherein the cross-section of the ring is adapted to the contours of the human body, and is preferably oval-shaped.

5. A device according to claim 4, wherein the ring has an axial width which varies around its periphery.

6. A device according to claim 5, characterized by an auxiliary ring having a greater diameter, which is adapted to be removably placed on the firstnamed or basic ring.

7. A device according to claim 6, wherein the auxiliary ring has an internal diameter such that it is adapted to be clamped onto that side of the basic ring having the larger external diameter.

8. A device according to claim 6, wherein the auxiliary ring is constructed as a protection ring adapted to snap onto that side of the basic ring having the larger diameter, and cover the portions of the condom which are in contact with the basic ring.

9. A device according to claim 6, wherein the axial width of the auxiliary ring is substantially larger than that of the firstnamed or basic ring.

10. A device according to claim 6, characterized by an apron of pliable material attached to the auxiliary ring.

11. A device according to claim 6, wherein the auxiliary ring is constructed as a plate-like element.

12. A device according to claim 9 characterized by a fluid absorbing pad, which is ring-like in shape and adapted to be placed around the male organ and which is impregnated with spermicidal and disease killing substances.

13. A device according to claim 6, wherein the ring or the auxiliary ring is covered on one or both sides by a skin imitating material.

14. A condom for use with the device according to claim 1, made of a thin elastic material and having an open end and a closed end, wherein the open end of the condom is provided with a number of circumferentially spaced tabs (with or without holes), loops or the like and/or the material of the condom in a portion of the condom adjacent to the open end being provided with a greater thickness than the remaining portion of the condom.

15. A condom for use with the device of claim 1, wherein the open end of the condom is provided with a thin widened collar which can be connected to the basic ring, and wherein the condom is preferably packaged in a zig-zag folded condition, and is provided, at least on its inner side, with a lubricant.

16. A device according to one of the claims 1 or 2, further comprises an elastic band, removably attached to the basic ring and adapted to be released from the ring and, at a place near the ring, be clamped onto the condom fit on the male organ.

17. A device according to claim 1 or 2, further comprises by an underpants to which the basic ring can be attached.

18. A device according to claims 1 or 2, further comprises a fluid absorbing pad, which is impregnated with spermicidal and disease killing substances, and which is removably attachable to the auxiliary ring or the plate-like element.

19. A device according to claims 1 or 2, further comprises an attachment ring adapted to be attached to the female and to which the basic ring can be removably attached.

20. A device according to claim 19, wherein the attachment ring is attached to the body of the female by a strap construction or the like.

* * * * *